United States Patent [19]

Nikolyukin et al.

[11] Patent Number: 5,710,012
[45] Date of Patent: Jan. 20, 1998

[54] SALT OF 6-CARBOXY-3-METHYLBENZOTHIAZOLONE HYDRAZONE HYDRATE IN COLORIMETRIC DETERMINATION OF HYDROGEN PEROXIDE

[75] Inventors: Yuri A. Nikolyukin, Donetsk, Ukraine; David J. Gibboni, Havertown, Pa.

[73] Assignee: ActiMed Laboratories, Inc., Burlington, N.J.

[21] Appl. No.: 450,780

[22] Filed: May 25, 1994

Related U.S. Application Data

[63] Continuation-in-part of Ser. No. 111,490, Aug. 25, 1993, Pat. No. 5,518,891.

[51] Int. Cl.$^6$ .................... C12Q 1/28; C07C 211/00
[52] U.S. Cl. .................. 435/28; 435/810; 436/904; 564/309
[58] Field of Search .............. 435/28, 810, 975; 436/135, 808, 904; 534/788; 548/161; 564/305, 309

[56] References Cited

U.S. PATENT DOCUMENTS

| | | | |
|---|---|---|---|
| 3,694,450 | 9/1972 | Wei | 260/294.8 C |
| 3,859,280 | 1/1975 | Wei | 260/240 G |
| 4,101,381 | 7/1978 | Klose et al. | 195/99 |
| 4,251,629 | 2/1981 | Yamanisi et al. | 435/28 |
| 4,260,679 | 4/1981 | Tsuda et al. | 435/10 |
| 4,492,754 | 1/1985 | Trager et al. | 435/28 |
| 4,672,029 | 6/1987 | Washburn et al. | 435/10 |
| 4,800,169 | 1/1989 | Bomer et al. | 436/166 |
| 4,837,308 | 6/1989 | Gerlach | 534/578 |
| 4,962,040 | 10/1990 | Hugl et al. | 436/135 |
| 5,043,269 | 8/1991 | Theodoropulos | 435/28 |
| 5,087,556 | 2/1992 | Ertinghausen | 435/7.9 |
| 5,094,943 | 3/1992 | Siedel et al. | 435/25 |
| 5,179,005 | 1/1993 | Phillips et al. | 435/14 |
| 5,234,813 | 8/1993 | McGeehan et al. | 435/7.9 |
| 5,453,360 | 9/1995 | Yu | 435/28 |
| 5,532,138 | 7/1996 | Singh et al. | 435/7.93 |

FOREIGN PATENT DOCUMENTS

| | | |
|---|---|---|
| 0068356 | 6/1982 | European Pat. Off. . |
| 0186134 | 12/1985 | European Pat. Off. . |
| 0201892 | 5/1986 | European Pat. Off. . |
| 0555045 | 2/1993 | European Pat. Off. . |

OTHER PUBLICATIONS

H.U. Bergmeyer: *"Methods of Enzymatic Analysis"* vol. I pp. 210–220 (3rd ed, 1983; Verlag Chemie).

*Primary Examiner*—Ralph Gitomer
*Attorney, Agent, or Firm*—Iver P. Cooper

[57] ABSTRACT

Water soluble salts of hydrazone compounds react quickly with aniline compounds in the presence of a peroxidase and hydrogen peroxide to provide a color which can be measured spectrophotometrically or visually, either in solution or when incorporated in a device for the measurement of analytes of interest. These water-soluble hydrazone salts are useful in determining hydrogen peroxide or an analyte which reacts to produce hydrogen peroxide in an aqueous liquid, by, in the presence of a substance having peroxidative activity, physically contacting a sample of a liquid with a dye-forming composition comprising a water-soluble salt of a hydrazone compound and a substituted or unsubstituted aniline compound to produce a colored dye; and detecting the dye formed as a result of the presence of hydrogen peroxide or an analyte which reacts to produce hydrogen peroxide.

20 Claims, 1 Drawing Sheet

SALT OF 6-CARBOXY-3-METHYLBENZOTHIAZOLONE HYDRAZONE HYDRATE IN COLORIMETRIC DETERMINATION OF HYDROGEN PEROXIDE

This application is a continuation-in-part of Ser. No. 08/111,490, filed Aug. 25, 1993,now U.S. Pat. No. 5,518,891, the entire contents of which are hereby incorporated by reference.

FIELD OF THE INVENTION

The present invention is directed to a reagent, method and apparatus for detection of hydrogen peroxide.

BACKGROUND OF THE INVENTION

Medical science has an increasing need for quick, accurate determination of analytes in blood or other body fluids. Traditionally, assays for analytes have been performed by laboratories and required skilled technicians, requiring complex apparatus and reagents, as well as considerable time in order to obtain accurate results. Numerous qualitative and some quantitative devices and methods have been developed which eliminate or decrease the need for laboratory diagnostic services. Many of these devices and methods include test strips or dip sticks which can be exposed to blood or another body fluid in order to obtain a diagnostic result. Common examples of this technology include the various test products for determining the concentration of glucose in diabetics, and determining cholesterol levels in blood.

Many clinical assays depend upon a detection and/or quantitative determination of hydrogen peroxide and compounds yielding hydrogen peroxide as a result of chemical or enzymatic reactions. For example, hydrogen peroxide is produced in the enzymatic assay of analytes such as glucose, cholesterol, uric acid, lipase, triglycerides, creatine kinase, etc. in the presence of oxygen. The quantity Of analyte present in a test sample is determinable from the amount of hydrogen peroxide produced and detected.

Known compositions for detecting or quantifying hydrogen peroxide in such assays generally comprise a substance having peroxidative activity, e.g., peroxidase, and a material which undergoes a detectable change (e.g., oxidation to a colored dye) in the presence of hydrogen peroxide and the peroxidative substance. Various materials which undergo such a detectable change include monoamines, diamines, phenols, leuco dyes and other known dyes or dye formers.

Hydrogen peroxide detection has also been accomplished by the reaction of a color-forming coupler and an oxidizable color developing compound, e.g., 4-amninoantipyrine, in the presence of peroxidase. Color-forming couplers which have been used for this purpose include N-substituted anilines, such as those described in U.S. Pat. No. 4,251,629, Yamanisi et al.; U.S. Pat. No. 4,260,679, Tsuda et al.; and U.S. Pat. No. 4,396,714, Maeda et al. Some of the anilines described in these references have solubilizing groups, such as hydroxy or sulfo groups, attached to the nitrogen atom.

Although the dye-producing materials which have been conventionally used are useful as indicators for hydrogen peroxide determination, there are instances when the concentration of hydrogen peroxide to be analyzed is too low to produce sufficient detectable color from such indicators. In some instances, this shortcoming can be overcome by using increased amounts of dye-forming materials. However, where the analyte concentration is initially low, or where high dilution of the test sample is required, such material may still provide insufficient detectable color in such instances.

The problem of low analyte concentration is particularly acute when analyte determination is attempted with a dry analytical element, such as described in U.S. Pat. No. 3,992,158, Przybylowicz et al.; U.S. Pat. No. 5,087,556, to Ertingshausen; and U.S. Pat. No. 5,234,813, McGeehan et al. In many of these types of devices, the indicator or reagent layer present in the device is very thin, and the concentration of the dye-forming material is necessarily quite low. Hence, the density of the color formed from low level analytes, or even from abnormally low concentrations of high level analytes, can be rather low.

For accurate quantitative determinations, the color formed from reaction of the color former should be an intense, easily discernible color, i.e., to permit easier reading, which is of some consequence for devices to be used by patients for self-monitoring, e.g., of blood glucose or cholesterol. Moreover, the reaction of hydrogen peroxide with the dye must be very rapid so that the color formed can be read by the user without delay. Since the ideal pH for effecting many enzymatic reaction is approximately 7, it is important that the compounds used be soluble in aqueous solution at a pH around 7.

Making quantitative determinations of analytes in body fluids for diagnostic purposes requires formation of a color and reading the endpoint. Greater color depth (higher molar absorptivity) of the color formed from the reaction of the indicator with a dye permits easier reading. Therefore, it has been desirable to develop dye systems that have very high molar absorptivity. Additionally, many of these devices are stored at room temperature over a period of months. Some of the currently used indicators have been found to degrade under long-term storage conditions, particularly in the presence of functional groups from other components of the device. High heat stability is necessary for long-term shelf life at 60° C. in dry form. One of the most commonly used indicators, 3-methyl benzothiazolone-2-hydrazone HCL, commonly known as MBTH.HCl, is insufficiently stable under such high heat conditions, as noted in U.S. Pat. No. 4,101,381.

Another problem with the conventionally used indicator MBTH is the relatively poor water solubility of the dye formed in the color reactions. This poor water solubility makes it difficult to remove all of the dye from the containers in an automatic analyzer, so that the method is poorly suited for use in continuous flow automatic analyzers. This effect is amplified in the oxidation procedure necessary for the development of the color, wherein secondary reactions occur in which an insoluble product is formed. In automatic analyzers, this product is deposited in the tubes and glass spirals, and thus further increases the carry over. Furthermore, this leads to an unstable, i.e., drifting, base line. In order to compensate for these disadvantages of MBTH as an indicator for automatic analyzers, the analysis time must be lengthened considerably, and the apparatus must be washed frequently. Lastly, allowances must be made for drifting of the base line.

Prior workers in the field have developed reagents for clinical assays which are based upon compounds related to MBTH, but none of these compounds has proved to be superior to MBTH. For example, Klose et al., in U.S. Pat. No. 4,101,381, disclose a reagent for detecting substances forming hydrogen peroxide using 3-methyl-2-sulfonyl-benzothiazolononhydrazone. Unfortunately, this compound has a much poorer solubility in water than MBTH, and thus cannot successfully be used in liquid assay systems.

Another disadvantage of using MBTH or its 2'sulfonated analog is that these dyes can only be used in systems at a pH below 7. Otherwise, an autoxidative color reaction can occur even in the absence of hydrogen peroxide, resulting in a relatively rapid coloration and thus of distinctly limited storage stability for a ready-to-use reagent.

Bomer et al., in U.S. Pat. No. 4,800,169, disclose decolorants for use in reagents for tests which contain single-component oxidation indicators. In this case, the decolorant prevents the appearance of a blank color value of the test aid. The decolorants do not couple with themselves, and they are not used with any coupling component. Esters of hydrozones are disclosed in Wei, U.S. Pat. Nos. 3,694,450 and 3,859,280. These compounds, however, are said to be central nervous system depressants, and there is no indication that these esters can be used as dyes for assays, either coupled or uncoupled.

SUMMARY OF THE INVENTION

Water soluble salts of 6-carboxy-3-methylbenzothiazolone hydrazone, or carboxy MBTH compounds have been found to react quickly with an aniline-type dye in the presence of a peroxidase and hydrogen peroxide to provide a color which can be measured spectrophotometrically or visually, either in solution or when incorporated in a device for the measurement of analytes of interest. The soluble salts of 6-carboxy-3-methylbenzothiazolone hydrazone hydrate, such as sodium potassium, or ammonium 6-carboxy-3-methylbenzothiazolone hydrazone hydrate, (NaCMBTH) have been found to be superior to MBTH.HCl in the speed of reactivity, long-term stability, solubility characteristics, and the molar absorptivity of the color these new compounds form with aniline-type dyes.

DETAILED DESCRIPTION OF THE INVENTION

Figure 1:
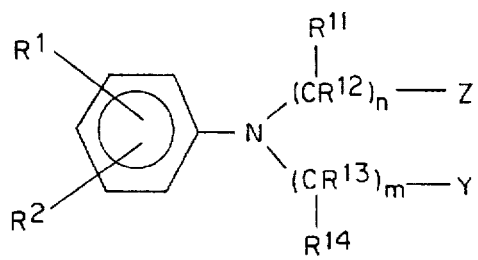
FIG. 1 shows examples of aniline compounds which can couple with the compounds of the present invention to form a dye.

The soluble hydrazone compounds of the present invention, in the presence of hydrogen peroxide, react rapidly with an aniline compound to form a deeply-colored compound. The dyes thus formed are useful in detecting compounds which can react to form hydrogen peroxide, particularly those compounds which react to form hydrogen peroxide as a result of the action of an enzyme, such as glucose in the presence of glucose peroxidase, or cholesterol in the presence of cholesterol oxidase. In the dyes formed from these soluble hydrazone compounds, the reaction to form a deeply-colored dye proceeds rapidly either on a substrate impregnated with the reactants or in solution.

The soluble salts of carboxy MBTH preferably have a molar extinction coefficient of at least 13,000 and preferably at least 15,000. The salts are soluble in cold water and rapidly form strongly colored dyes with aniline compounds in the presence of hydrogen peroxide. Dye formation with the compounds of the present invention occurs over a wide pH range, generally from about 4 to about 11.

Assays

The compounds of the present invention can be used in both solution and dry element assays. The compounds can be formulated with optional substances having peroxidative activity or a buffer which maintains the pH of the composition in an aqueous environment at a pH of from about 4 to 11.

Substances having peroxidative activity useful in the practice of the present invention are also known as peroxidative substances, and are capable of catalyzing the oxidation of another substance by means of hydrogen peroxide or another peroxide. Such substances include natural and synthetic peroxidases, cytochromes, hemin, forms of hemoglobin, alkaline hematin, iron sulfocyanate, iron tannate, tungstic acid and its salts, molybdic acid and its salts, chromic salts and the like. Peroxidase is a particularly useful peroxidative substance. A catalytic amount of the peroxidative substance can be used in a reagent formulation, as is well known to those skilled in the art.

Substantially any buffer can be used in the composition of this invention which does not interfere with the assay and which maintains the composition at a pH which is conducive to dye formation as well as to the reactions required for a given assay. Generally, the pH is maintained within the range of from about 4 to about 11, but a specific pH depends upon the particular analyte being assayed and the reagents used therein. An advantage of the instant dye is that it can be used in systems at a pH of 7 or above. For example, when a fluid is assayed for uric acid using uricase, the pH of the composition is preferably maintained between about 8 and 9. However, the instant dye may be used in a acidic system (pH<7) as well. For example when a sample is assayed for glucose using glucose oxidase, the pH of the composition is generally maintained between about 4 and about 7. Useful buffers for various assays include carbonates, borates, phosphates, maleates, glutarates, the tris materials, such as tris(hydroxy-methyl)aminomethane, and others known in the art. One of the advantages of the compounds of the present invention is that they are readily soluble and rapidly couple with aniline compounds at a pH of between about 4 and 11, which is the pH range at which most clinical assays are conducted.

Compositions for assays can be prepared for use in a solution assay by mixing the soluble hydrazone compound with an oxidizable color developing compound such as an aniline dye. Additional materials can be mixed in as needed.

The molar ratios of soluble hydrazone compound to aniline compound preferably range from about 20:1 to about 1:20, with more nearly equimolar ratios being more preferred for the optimum combination of detection sensitivity and interference resistance. When the compounds of the present invention are used in solution assays, the soluble hydrazone compound is preferably present in a concentration of up to about $10^{-3}$ molar, and more preferably from about $5 \times 10^{-5}$ to about $5 \times 10^{-4}$ molar. The aniline compound is preferably present in an amount sufficient to react with the soluble hydrazone compound, such as a molar ratio of from about 20:1 to about 1:20, and more preferably about equimolar. For example, the aniline compound is preferably present in an amount of up to about 10 millimolar, and preferably from about 0.5 to about 2 millimolar. The amounts of the optional components of the composition, e.g., buffer, surfactant, peroxidative substances, etc., are within the skill of a worker in the art. Cf. U.S. Pat. Nos. 4,492,754; 4,672,029; 5,179,005; 5,043,269, all of which disclose clinical assays reciting varying amounts of such optional components as required by the individual assay.

The soluble hydrazone compounds of the present invention can be used to determine an analyte which is capable of producing hydrogen peroxide (i.e., analyte which can participate in a reaction or series of reactions which produce hydrogen peroxide) in an fluid sample.

The sample may be a biological fluid or a non-biological fluid. Non-limiting examples of biological fluids obtained in vivo include whole blood, a separated blood fraction, urine, semen, saliva, cerebrospinal fluid, amniotic fluid, ascites fluid, pleural effusion, cyst fluid, pus, tissue extracts, etc. Non-limiting examples of biological fluids obtained in vitro include tissue culture supernatant, such as that of hybridoma cells, or microbial fermentation medium.

The sample may also be a non-biological fluid such as drinking water, wastewater, groundwater, or a nonaqueous fluid.

This composition can be used with the appropriate interactive reagent or combination of reagents which produces hydrogen peroxide upon interaction with the analyte during the assay. Analytes which can be determined in this matter include glucose, triglycerides, uric acid, lipase, cholesterol, galactose, amino acids, creatine kinase, and others known to those skilled in the clinical chemistry art. For example, to determine uric acid, the composition is used with uricase. To determine cholesterol, the composition is used with cholesterol oxidase and cholesterol ester hydrolase. Other interactive compositions can be fashioned for a given analyte by one skilled in the art. The amounts of the reagents suitable for a given assay are known to one skilled in the art of clinical chemistry. In the context of the present disclosure, determination means either qualitative (i.e., merely detection), semi-quantitative, or quantitative analysis unless otherwise specified.

Aniline Dyes

The soluble hydrazones of the present invention can be coupled with any type of aniline dye, i.e., any dye which includes an amino group bonded to a phenyl group. The substituents on the phenyl or amino group can be chosen to change the $\lambda_{max}$ of the dye or to change the visible color for optical or spectrophotometric determinations.

Preferably, the soluble hydrazone is coupled with an aniline having the formula given in FIG. 1, where $R^1$ and/or $R^2$ can be H; $C_1$–$C_9$ alkyl; $C_1$–$C_9$ alkoxy; $NR^3R^4$ where $R^3$ and/or $R^4$ are H, $C_1$–$C_9$ alkyl, aryl or heteroaryl; F; Cl; Br; I; $COOR^5$ where $R^5$ is H, $C_1$–$C_9$ alkyl, aryl or heteroaryl; CN; $CONR^6R^7$ where $R^6$ and/or $R^7$ are H, $C_1$–$C_9$ alkyl, aryl or heteroaryl; aryl; aryloxy; heteroaryl, heteroaryloxy; and $R^{11}$, $R^{12}$, $R^{13}$ and/or $R^{14}$ are H; $C_1$–$C_9$ alkyl; $C_1$–$C_9$ alkoxy; $NR^{15}R^{16}$ where $R^15$ and/or $R^16$ are H, $C_1$–$C_9$ alkyl, aryl or heteroaryl; F; Cl; Br; I; $COOR^{17}$ where $R^{17}$ is H, $C_1$–$C_9$ alkyl, aryl or heteroaryl; CN; $CONR^{18}R^{19}$ where $R^18$ and/or $R^19$ are H, $C_1$–$C_9$ alkyl, aryl or heteroaryl; aryl; aryloxy; heteroaryl, heteroaryloxy; or any other group that does not interfere with the coupling reaction; and n is an integer of from 0 to 10; and Z and/or Y is H; OH; SH; $COOR^8$ where $R^8$ is H, $C_1$–$C_9$ alkyl, aryl or heteroaryl; CN; $CONR^9R^{10}$ where $R^9$ and/or $R^{10}$ are H, $C_1$–$C_9$ alkyl, aryl or heteroaryl; $NR^{20}NHR^{21}$ where $R^{20}$ and/or $R^{21}$ are H, $C_1$–$C_9$ alkyl, aryl or heteroaryl; and at least one of Z and Y is $COOR^8$, $CN_1NR^9R^{10}$ or $NR^{20}NHR^{21}$.

The term "aryl" includes substituted and unsubstituted single, plural and fused ring groups which have aromatic bonding, including but not limited to phenyl, naphthyl, biphenyl, fluoryl, pyryl, and the like. Substituents on the aryl ring may be any substituents which do not interfere with coupling to the soluble hydrazones of the present invention, including but not limited to $C_1$–$C_5$ alkyl, $C_1$–$C_5$ alkenyl, F, Cl, Br, I, hydroxyl, $C_1$–$C_5$ alkoxy, CN, $COOR^1$, $CONR^6R^7$, and any combinations thereof. Likewise, the alkenyl and alkyl groups may be substituted by F, Cl, Br, I, hydroxyl, CN, and other groups which do not interfere with the coupling.

The term "heteroaryl" encompasses rings having aromatic bonds having at least one heteroatom in the ring. The heteroatoms may be N, S, or O, and any combination thereof. Non-limiting examples of the heteroaryl groups which can be included in the amines which can be coupled to the soluble hydrazones of the present invention are pyridine, quinoline, isoquinoline, pyrazine, pyrimidine, purine, oxathialone, oxazole, dithiazine, indole xanthene, acridine and the like. These heteroaryl groups may likewise be substituted at one or more positions by at least one substituent selected from the group consisting of $C_1$–$C_5$ alkyl, $C_1$–$C_5$ alkenyl, $C_1$–$C_5$ alkoxy, CN, $COOR^1$, $CONR^6R^7$, and the like.

The above aniline compounds are disclosed and described in more detail in application Ser. No. 08/111,490, filed Aug. 25, 1993, now U.S. Pat. No. 5,518,891 the entire contents of which are hereby incorporated by reference.

Among the aniline dyes that can be used to form dyes according to the present invention are the following:

N,N-(biscarboxymethyl)aniline (PAGA)

N,N-(biscarboxymethyl)-4-methyoxyaniline (MOPAGA)

N,N-(bis-β-carboxyethyl)aniline (PAPA)

N-ethyl-N-phenylglycine (EPG)

N-ethyl-N-carboxyethylaniline (NENCEA)

N-phenylpiperidinyl succinate (PPS)

N-ethylanilinopropaneamine (NEAP)

N-methylanilinopropaneamine (NMAP)

N-methyl-N-carboxyethylanilin (NMNCEA)

N,N-(bis-β-carboxyethyl )-2,5-dimethylaniline (BCEDMA)

N-β-carboxyethylaminobenzoic acid (NCEABA)

Compounds of the formula:

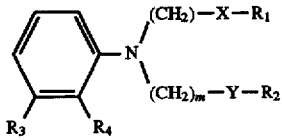

wherein n and m are individually selected from whole numbers 1 to 4,

X and Y, which can be the same or different, represent a valence bond or a phenylene radical, $R_1$ and $R_2$ are individually selected from carboxyl or sulfonic acid groups and one of $R_1$ and $R_2$ can also be hydrogen or lower alkyl, and $R_3$ and $R_4$ are individually selected from hydrogen and alkyl radicals of up to 6 carbon atoms.

Test means prepared with dyes made according to the present invention, and test systems employing these test means, are preferably used in a generally neutral or slightly acid pH range, although the dyes remain operative even at a somewhat higher pH up to almost pH11. The maintenance of a generally neutral or acid pH provides improved reactivity in terms of speed and resistance to interference. The soluble hydrazones of the present invention are particularly well suited to clinical assays because they react quickly with aniline compounds at approximately neutral pH to produce dyes having high molar absorptivity.

The soluble hydrazones of the present invention react with aniline compounds in the presence of hydrogen peroxide. Many analytes, including glucose, cholesterol, uric acid, etc. produce hydrogen peroxide when acted upon by a peroxidase enzyme, i.e., an enzyme which will catalyze a reaction wherein hydrogen peroxide oxidizes another substance. The peroxidases are generally conjugated proteins containing iron porphyrin. Peroxidase occurs in horseradish, potatoes, figtree sap and turnips (plant peroxidase); in milk (lacto peroxidase); and in white blood corpuscles (verdo peroxidase). Peroxidase also occurs in microorganisms and may be produced by fermentation. Certain synthetic peroxidases, such as those disclosed by Theorell and Maehly in *Acta. Chem. Scand.* Vol. 4, pages 422–434 (1950), are also satisfactory for use in hydrogen peroxide detection systems. Less satisfactory but also useful are substances such as hemin, methemoglobin, oxyhemoglobin, hemoglobin, hemochromogen, alkaline hematin, hemin derivatives, and certain other compounds which demonstrate peroxidative or peroxidase-like activity.

Other substances which are not enzymes but which demonstrate peroxidative activity and could be used as oxidizers are iron sulfocyanate, iron tannate, ferrous ferrocyanide, chromic salts (such as potassium chromic sulfate) absorbed in silica gel, etc.

Among the analytes that can be determined by detecting hydrogen peroxide produced by action of an oxidizing agent on the analyte are glucose, cholesterol, uric acid, cholesterase, phospholipids, creatine or creatinine. All of these assays can readily be conducted using the dye formed according to the present invention.

In the present invention, the term "reagent layer" is used to refer to a layer in which an analyte is converted into a visually detectable species in the presence of a dye composition according to the present invention. This basically comprises a substance having peroxidase activity and a substance capable of causing a detectable change in the presence of hydrogen peroxide and the substance having peroxidase activity. In this case, the substance capable of causing a detectable change in the presence of hydrogen peroxide and the substance having peroxidase activity is the combination of the soluble hydrazone compound of the present invention and an aniline compound.

In use, the reagent, i.e., the substance which reacts with the analyte of interest to form hydrogen peroxide, can be incorporated in an assay device with the dye-forming substance, or can be in a layer separate from the dye-forming substance. The formation of a colored dye with the soluble hydrazone compound and the aniline compound indicates the presence and/or concentration of a desired analyte, or a reaction or decomposition product of the analyte.

The term "substance having peroxidase activity" is used herein to mean a substance which catalyzes oxidation of a hydrogen donor with hydrogen peroxide (as a substrate) and is well recognized in the art. Examples of substances having peroxidase activity include peroxidases extracted from various organisms, synthetic peroxidase and other chemical substances extracted from organisms which exhibit an activity similar to that of peroxidase. Of these, horseradish peroxidase is preferred.

In a test device, a color-forming reaction layer can contain an analyte component which differs from hydrogen peroxide, which is hereinafter referred to as an "analyte precursor component", and a reagent composition system capable of forming hydrogen peroxide through chemical reaction. Alternatively, a reagent layer containing the reagent system for forming hydrogen peroxide can also be provided separately from the reagent layer or any other layer in the test device.

The hydrogen peroxide forming reagent layer can be any reagent composition system in which hydrogen peroxide is produced from the analyte precursor component through chemical reaction in one step or a reagent composition system in which hydrogen peroxide is produced from the analyte precursor components through chemical reaction comprising continuous enzyme reactions. One example of such a reaction is, for example:

Depending upon the hydrogen peroxide-forming reagent system, the reagent system for forming hydrogen peroxide can be incorporated into the reagent layer, the color-forming reaction layer or the dye-fixing layer, or a single layer or a plurality of layers different from the aforesaid layer can be provided as the hydrogen-peroxide forming layer.

The dye-forming formulation of the present invention can be incorporated in a dry analytical element such as a multilayer assay device, which generally comprises an absorbent carrier material, i.e., a self-supporting absorbent sheet or pressed material, such as filter paper or strips, which contains the analytical composition and, optionally, any other desired reagents such as the peroxidative substances.

When used in a dry multilayer assay device, the dye-forming composition can be incorporated into a suitable carrier material by imbibition, impregnation, coating, or by immobilization onto an insoluble matrix. Useful carrier materials are those which are insoluble and maintain their structural integrity when exposed to water or physiological fluids such as urine or serum. Useful elements can be prepared from paper, porous particulate structures, cellulose, wood, glass fibers, woven and nonwoven fabrics (both synthetic and nonsynthetic) and the like. A useful dry analytical device is made by imbibing a solution of the analytical composition into the material and drying.

The components of the analytical composition, as well as the peroxidative substance, interactive component, etc., can be incorporated in any of the element zones. The location of individual components is well within the skill of a worker in the clinical chemistry art.

The composition and method of the present invention can also be used with a dry analytical element which contains an absorbent carrier material, i.e., a thin sheet of a self-supporting, absorbent or bibulous material, such as filter paper or strips, which contains the composition of the present invention. Preferably, these elements also contain a peroxidative substance. These elements, which generally provide qualitative assays, are known in the art as test strips, dip sticks, and the like.

When employed in dry chemistry elements, the composition can be incorporated into a suitable absorbent carrier material by imbibition, impregnation, coating or others suitable technique. Useful absorbent materials are insoluble and maintain their structural integrity when exposed to water or physiological fluids such as urine or serum. Useful elements can be prepared from paper, porous particulate structures, porous polymeric films, cellulose, wood, glass fiber, woven and nonwoven fabrics (synthetic and natural) and the like. Useful materials and procedures for making such elements are well known in the art, and many are described in the following U.S. Pat. Nos.: 3,092,465; 3,802,842; 3,915,647; 3,917,453; 3,936,357; 4,248,829; 4,255,384; 4,270,920; 4,312,834; 5,087,556; and 5,234,813; the entire contents of which are hereby incorporated by reference.

Preferably, the dry analytical elements of the present invention have at least one porous spreading zone as a carrier material. This zone can be self-supporting, i.e., composed of a material rigid enough to maintain its integrity, but preferably it is carried on a separate supporting substrate, commonly called a support. This support can be any suitable dimensionally stable, and preferably radiation transmissive, material which transmits electromagnetic radiation of a wavelength between about 200 and about 900 nm. A support of choice for a particular element should be compatible with the intended mode of detection (reflection or transmission spectroscopy). Useful support materials include paper, metal foils, polystyrene, polyesters such as polyethylene terephthalate, polycarbonate, cellulose esters, and the like.

The porous spreading zone can be prepared from any suitable fibrous or non-fibrous material or mixtures of either or both. The void volume and average pore size of this zone can be varied depending upon the use intended. For example, if whole blood or other liquid samples containing high molecular weight materials are to be assayed, the void volume and average pore size are generally greater than if serum or urine is to be analyzed.

Useful spreading zones can be prepared using fibrous materials, either mixed with a suitable binder material or woven into a fabric, as described by Kitajima et al. in U.S. Pat. No. 4,292,272. Alternatively, the spreading zone is prepared from polymeric compositions such as blush polymers or particulate material, with or without binding adhesives. Other useful spreading zone materials are described in German OLS No. 3,150,102 and Japanese Patent Publication No. 57-101760. It is desirable that the spreading zone be isotopically porous, meaning that the porosity is the same in each direction in the zone as created by interconnected spaces or pores between particles, fibers, polymeric strands, etc.

The elements can have more than one zone, e.g., reagent zones, spreading zones, registration zones, mordant zones, radiation-blocking or filter zones, subbing zones, barrier zones, buffer zones, etc. The zones are generally in fluid contact with each other, meaning that fluids, interactive reagents and reaction products such as colored dyes can pass between superposed regions of adjacent zones. Stated in another manner, fluid contact refers to the ability to transport components of a fluid between the zones in fluid contact. Preferably, the zones are separately coated layers, although two or more zones can be part of a single layer, or a zone can contain two or more separate layers. The compounds of the present invention can be incorporated in any of the zones of the elements that would be suitable for the particular analysis. The location of other reagents or addenda can be any suitable zone known by a worker skilled in the art of clinical chemistry.

In the elements of the present invention, the amounts of the soluble hydrazone compound and other reagents can be varied widely depending upon the analyte to be determined. Preferably, the soluble hydrazone compound is present to provide a coverage of from about 0.2 to about 3 gram/m$^2$. The peroxidative substance can be present in a coverage within the skill of a worker in the art. For peroxidase, for example, the coverage is preferably up to about 150,000 and more preferably from about 40,000 to about 60,000 IU/m$^2$. A variety of other desirable, but optional, reagents and addenda can be present in the element in amounts known to one skilled in the art. These materials include surfactants, buffers, binders, pigments, activators, interactive reagents, etc. In the context of this application, IU represents the International Unit for enzyme activity required to catalyze the conversion of 1 µmole of substrate per minute under standard pH and temperature conditions for the given enzyme.

In one embodiment of an apparatus for use with the soluble carboxy MBTH compounds of the present invention, a self-contained chromatic quantitative analyzer is used for quantitatively detecting an analyte in a biological fluid. The device includes a base having a first open reservoir for receiving the bio-logical fluid. A means for separating solids from the bio-logical fluid is provided in the first open reservoir. The second open reservoir draws the biological fluid from the channel by capillary and/or wicking action and, when the second open reservoir is filled with the biological fluid, the capillary and/or wicking action terminates. A membrane is provided in the channel which is permeable to the biological fluid. There is at least one chromatic chemical indicator immobilized in the membrane in a predetermined concentration. The membrane enables biological fluid to interact with the chromatic chemical indicator. Such a device is described in detail in U.S. Pat. No. 5,087,556, the entire contents of which are hereby incorporated by reference.

In a preferred apparatus for use in the present invention, the analytical device used includes a fluid sample well means connected to a sample initiation area in such a fashion that the assay will not commence unless sufficient sample is introduced into the sample well means to conduct the assay. Once sufficient sample has been deposited into the sample well means, the sample flows into an initiation area and the assay commences. Such a device is described in U.S. Pat. No. 5,234,813, the entire contents of which are hereby incorporated by reference.

In one embodiment of a device which can be used with the solubly hydrazone compounds of the present invention, a fluid sample measuring device comprises three distinct parts:

(a) a sample well into which sample is introduced so as to meter the sample to ensure that sufficient sample is present to conduct an assay;

(2) an assay initiation area located at a level above the sample well; and (3) siphon means for connecting the sample well and the assay initiation area by which liquid can readily flow, resulting in a siphoning action from the sample well to the assay initiation area.

The assay initiation area is connected to a detection zone where the actual assay occurs. This detection zone includes an indicator means, including at least one of the soluble hydrazone compounds of the present invention, which develops a detectable signal such as a color. The detectable portion of the detection zone caused by reaction of the indicator means with the analyte, or a derivative thereof, as observed after the capillary action is terminated, corresponds to the concentration of the analyte in the fluid sample. A scale is provided along the length of the detection zone channel to readily equate the detectable portion of the channel to the concentration of analyte.

The amount of the dye-forming components can be varied widely. Preferably, the soluble hydrazone is present in an amount of coverage of at least about 100, and more preferably from about 300 to about 5000 mg/m$^2$. The aniline compound is preferably present in an amount of coverage of at least about 100, and more preferably from about 1000 to about 5000 mg/m$^2$. The peroxidative substance can be present in a coverage preferably of at least about 25,000, and more preferably from about 50,000 to about 100,000 I.U./m2 for peroxidase. A variety of other desirable but optional reagents and additives can be present in the elements in amounts known to one skilled in the art. Such materials include surfactants, buffers, binder, pigments, activators, reagents of interactive compositions, etc.

To quantify an analyte using such a device, a fluid sample is deposited into the sample well means. If there is sufficient volume of sample to conduct an assay, the sample is drawn up into the assay initiation area through the siphon means. There may be a separation zone below the assay initiation area to remove any solids suspended in the fluid sample. The fluid sample is then drawn through the detection zone by capillary and/or wicking action, preferably to a reservoir means, which contains an absorbent. The reservoir means draws the fluid sample through the detection zone and, when the reservoir is filled with the fluid sample, the capillary and/or wicking action is terminated. While the fluid sample is being drawn through the detection zone, the indictor means is permeated with the fluid sample. The detection zone includes a suitable indicator immobilized therein in a predetermined concentration to react with the analyte. Thus, the analyte in the fluid sample is completely reacted in a single step or a series of chemical reactions with the indicator means.

Determination of hydrogen peroxide or an analyte is achieved when the soluble hydrazone compound and the aniline compound react to form a dye. This dye can be detected with the unaided eye or with suitable spectrophotometric means and procedures, preferably at a wavelength greater than or equal to 600 nm. The substituents on the soluble hydrazone as were as on the aniline compound can be chosen to provide a dye with an absorption maximum at any desired wavelength. One skilled in the art of dye chemistry can readily determine which substituents should be present on the soluble hydrazone compound and/or aniline compound to achieve a dye with the desired maximum absorbance.

The composition and method of the present invention are adaptable to solution as well as to dry element assays. In a solution assay, generally the chromogenic composition (optionally containing interactive reagents) is physically contacted and mixed with a liquid test sample in a suitable container, such as a test tube, Petri dish, beaker, cuvette, etc. The resulting solution is incubated for a relatively short time, generally less than about five minutes, at a suitable temperature, such as 37° C. The sample is then evaluated by measuring the amount of dye provided upon reaction of the color-forming coupler with color developing compound in the presence of hydrogen peroxide. The amount of dye can then be correlated to the amount of hydrogen peroxide either initially present in the sample or produced as a result of the presence of an analyte. Such an evaluation can be effected visually or with suitable colorimetric detection equipment and procedures.

The color-forming coupler and color developing compound can be provided as part of a diagnostic test kit for either dry or solution assays. For solution assays, the kit components can be supplied as lyophilized reagents in individual packets having predetermined amounts. Alternatively, they can be provided in bottled or otherwise packaged solutions sufficient in size for one or more assays. Other reagents or non-reactive addenda can also be supplied in the kit along with suitable assay utensils or containers for performing the assay, if desired. A dry analytical element, such as one of those described below, containing one or more reagents necessary for an assay can also be included as part of a diagnostic test kit.

When the kit is to be employed in an analysis, the components are mixed together, dissolved in or diluted with water as necessary, and employed to effect the intended analysis by generally known techniques. That is, the various ingredients are mixed with the sample to be analyzed, and the resulting mixture is held at a predetermined temperature to permit the dye of the present invention to form. The concentration of the dye is then determined, as by conventional photometric analysis. These analyses may be performed manually or automatically using equipment and techniques already well known to the art.

Assays for analytes using the dye composition of the present invention can be manual or automated. In general, using dry elements containing reagents including the soluble hydrazone compounds of the present invention, hydrogen peroxide or analyte determination is made by taking the element from a supply roll, chip packet, or other source and physically contacting it with a sample of the liquid to be tested. This contact can be accomplished in any suitable manner, including dipping or immersing the element into the sample or, preferably, spotting the element by hand or machine With a drop of the sample using a suitable dispensing means. After sample application, the element is left for a period of generally less than five minutes while any hydrogen peroxide formed from the analyte in the sample causes the soluble hydrazone to couple with the aniline compound to form a dye. This dye can be detected with the unaided eye or with suitable spectrophotometric means and procedures. Alternatively, for a quantitative assay, the element can be designed so that a color bar is formed which is proportional to the amount of hydrogen peroxide in the sample or formed by the analyte in the sample with the peroxidative agent.

The following examples are given for purposes of illustration only, and are not meant to be limiting of the scope of the invention. Although the examples given here are for the preparation of 3-methylbenzothiazolone-2-hydrazone-6-carboxylic acid, sodium salt, other soluble salts according to the present invention can be prepared using processes known to a synthetic organic chemist.

Example 1

Preparation of 2-aminobenzothiazole-6-carboxylic acid

Figure 2:
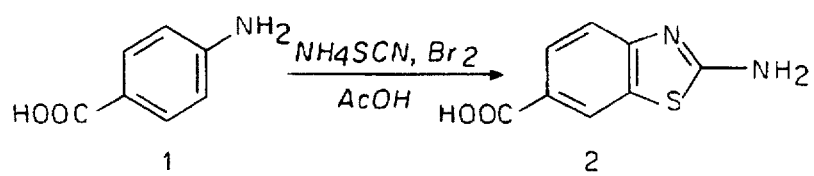
FIG. 2 shows the preparation of 2-aminobenzothiazole-6-carboxylic acid from 4-aminobenzoic acid.

As shown in FIG. 2, 2-aminobenzo-thiazole-6-carboxylic acid, 2, is prepared from 4-aminobenzoic acid and ammonium thiocyanate in the presence of bromine and glacial acetic acid. One hundred thirty seven grams of 4-aminobenzoic acid was slurried with 70 mL of acetic acid in a 500 mL RB flask which was cooled in a water bath to 5°–10° C. Then, 30.4 grams of ammonium thiocyanate was added to the slurry, followed by an additional 70 mL of glacial acetic acid. Next, 11.2 mL of bromine diluted in 30 mL of glacial acetic acid was added dropwise over a 30-minute period. After the bromine was completely added, the slurry was allowed to warm to room temperature and was stirred at room temperature for 30 minutes. After stirring at room temperature, the reaction mixture was transferred to a 1-L Erlenmeyer flask, and 400 mL of water was added.

The aqueous mixture was heated to boiling (95°–100° C.) and allowed to stir at boiling for 15 minutes. The reaction mixture was filtered while hot, and the residue discarded. The clear-orange-colored filtrate was stored at 4° C. in a refrigerator until cool and a precipitate had formed. The precipitate was slurried in 800 mL water and neutralized with 190 mL ammonium hydroxide to pH 6 as measured by litmus. The precipitate formed was collected in a Büchner funnel, and when sucked dry gave a wet weight of about 290–300 grams of crude product. The crude product was slurried in 400 mL water and the pH of the slurry was adjusted to 10 by the addition of 30 mL of 30% sodium hydroxide. The resulting turbid solution was filtered and the residue discarded.

The filtrate was cooled to room temperature and neutralized while cooling in a ice/water bath to pH 6 by the addition of 17–20mL acetic acid. The resulting aqueous suspension of precipitate was cooled at 4° C. overnight. After fully cooling and settling, the precipitate produced was collected in a Büchner funnel and sucked dry. The purified product was dried in air for 24 hours. The yield was 34.3 grams (88%) of a yellow, grainy solid.

Elemental analysis:
Calcd: C, 49.48%; H, 3.09%; N, 14.43%; S, 16.49%
Found: C, 49.26%; H, 3.09%; N, 14.01%; S, 16.22%
HPLC $C_{18}$ column, 250 mm×5 μm; phosphate buffer/acetonitrile mobile phase. RT=9.75 min.

Preparation of 2-amino-3-methyl-6-carboxybenzothiazolium iodide

Figure 3:
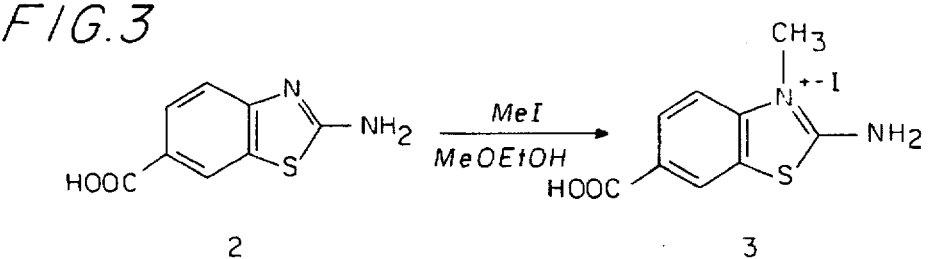
FIG. 3 shows the preparation of 2-amino-3-methyl-6-carboxybenzothiazolium iodide from 2-aminobenzothiazole-6-carboxylic acid.

As shown in FIG. 3, 2-amino-3-methyl-6-carboxybenzothiazolium iodide, 3, is produced from compound 2 above. Thirty four grams of 2-amino-6-carboxybenzothiazole was placed in a 2-L RB flask and slurried with 400 mL of methoxyethanol. Methyl iodide was added all at once, and 425 mL more methoxyethanol was added. The flask was fitted with a condenser and the reaction mixture was brought to reflux. The mixture was refluxed for fourteen hours. The resulting dark amber solution was cooled to room temperature and poured into one liter of diethyl ether, out of which a precipitate formed. The precipitate was collected in a Büchner funnel and washed with 800mL ether. It was dried in the air with gentle warming. The yield was 36.5 grams (62%) of a pale yellow solid with purple tinges.

Elemental analysis:
Calcd.: C, 32.14; H, 2.68; N, 8.33; S, 9.52; I, 37.80
Found: C, 32.17; H, 2.64; N, 8.17; S, 9.43; I, 37.68
HPLC $C_{18}$ column, 250 mm×5 μm; phosphate buffer/acetonitrile mobile phase. RT=2.24 min.

Preparation of 3-methylbenzothiazolone-2-hydrazone-6-carboxylic

Figure 4:
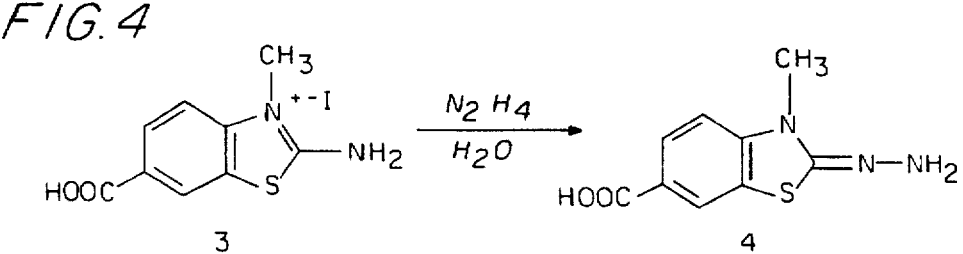
FIG. 4 shows the preparation of 3-methylbenzothiazolone-2-hydrazone-6-carboxylic acid from 2-amino-3-methyl-6-carboxybenzothiazolium iodide.

As shown in FIG. 4, CMBTH, 4 is prepared from compound 3.

2-Amino-3-methyl-6-carboxybenzothiazolium iodide (36.5 g) was placed into a 500-mL RB flask and slurried in 170 mL water. The slurry was dark purple. Hydrazine hydrate (26.5 mL) was added all at once, and the slurry decolorized immediately. One hundred mL additional water was added and the mixture was brought to reflux. The reaction mixture was refluxed with stirring for one hour and filtered while hot. The residue was discarded and the filtrate neutralized to pH 6 with 27 mL glacial acetic acid. The aqueous suspension was refrigerated overnight. The product was collected in a Büchner funnel and sucked dry. The crude wet weight was about 135–140 grams.

Elemental analysis
Calcd.: C, 45.00; H, 4.17; N, 17.50; S, 13.33
Found: C, 44.81; H, 4.11; N, 18.80; S, 13.79
HPLC $C_{18}$ column, 250 mm×5 μm; phosphate buffer/acetonitrile mobile phase. RT=2.24 min.

NMR
($D_2O$) 8.10, s, 1H, aryl H; 7.97, d, 1H, aryl H; 3.6, s, 3H, N-Me

Preparation of 3-methylbenzothiazolone-2-hydrazone-6-carboxylic acid, sodium salt (NaCMBTH)

Figure 5:
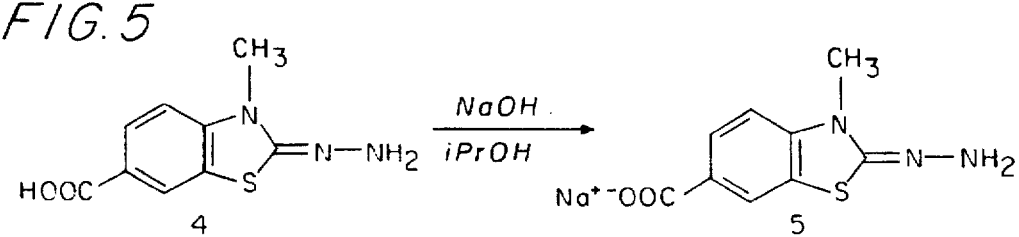
FIG. 5 shows the preparation of 3-methylbenzothiazolone-2-hydrazone-6-carboxylic acid, sodium salt, from 3-methylbenzothiazolone-2-hydrazone-6-carboxylic acid.

As shown in FIG. 5, NaCMBTH, 5, is produced from CMBTH, 4.

One hundred eighteen grams of wet crude 3-methylbenzothiazolone-2-hydrazone-6 carboxylic acid was slurried in sufficient water to allow stirring in a 600-mL beaker. The mixture was heated to 70° C. Then, 15.5 mL sodium hydroxide solution was added by pipetful until the pH was 10. Insoluble matter was filtered out and the clear filtrate was cooled to room temperature and transferred to a 500-mL Erlenmeyer flask. Isopropanol was carefully pipetted onto the caustic solution so that there was a two phase system, after which the flask was cooled quickly in an ice-salt bath. The contents of the flask were swirled to mix the two phases and to allow crystallization to begin. Cooling continued as more isopropanol was pipetted into the flask to complete precipitation of the product. The resulting precipitate was collected in a Büchner funnel. The yield of the sodium salt was 75.3 grams wet. The crude product was slurried in 250 mL isopropanol, collected on a Büchner funnel, then resuspended in 250 mL ether and recollected on a Büchner funnel. The clean product was dried in air and stored in the dark in an airtight container.

Elemental analysis:
Calcd.: C, 35.06; H, 4.87; N, 13.64; S, 10.39
Found: C, 35.12; H, 4.77; N, 13.80; S, 10.06
HPLC $C_{18}$ column, 250 mm×5 μm; phosphate buffer/acetonitrile mobile phase. RT=2.25 min.

TGA
% volatiles ranges from around 5% to around 19%, depending upon degree of hydration.

Example 2

Relative Molar Extinction Coefficients

The relative absorbance of MBTH and sodium carboxy MBTH, an illustrative soluble hydrazone compound, was measured and compared. Since each compound was measured at the same molar concentration, the molar extinction was proportional to the concentration.

Each sample contained the following:

1 mL phosphate buffer, 0.035M, pH 6.5

10 μL R-MBTH solution, 10 mM, where R=H or COONa

100 μL N-ethylanilinopropanamine hydrochloride, 10 mM

10 μL POD solution, ~120 IU/mL

50 μL $H_2O_2$, 20 mM

A 1-mL aliquot of each solution was transferred to a cuvette and diluted with an addition 2 mL of phosphate buffer solution. Absorbance at 600 nm was read:

| | |
|---|---|
| MBTH.HCl | 0.1513 absorbance units |
| CMBTH | 0.2115 absorbance units |

Example 3

Heat Stability of CMBTH

In order to evaluate the heat stability of sodium carboxy MBTH, 38 mg. of either MBTH.HCl or NaCMBTH was added to 1.2 mL water to dissolve. Then, 0.75 mL of this solution was added to 21 mg Hydrisel SX 660, a commercial surfactant and 1015 mL 0.1% ACP polymer (ISP Technologies), prepared in 70% isopropanol solution. Each solution was coated onto a 4-inch wide polyester fabric in a thin layer and dried at 40° C. for fifteen minutes. The coated fabric was sealed in an airtight foil bag and stored at 4° C.

Small samples (2 cm×5 cm) of each coated fabric were placed into a 120° C. oven and removed at appropriate intervals. The heat-stressed fabric samples were assayed spectrophotometrically.

The fabric samples were placed into a tared test tube and weighed. Ten mL of 20 mM phosphate buffer, pH 7.0, was added. The tubes were capped and agitated for ten minutes at room temperature. Absorbance at 310 nm was read for each sample and the values were compared against a standard curve. Table 1 shows the comparative densities for the two compounds after being held at 120° C. for periods.

TABLE 1

| Time @120° C. | Density of NaCMBTH (mg/m$^2$) | Density of MBTH.HCl (mg/m$^2$) |
|---|---|---|
| 0 | 75.4 | 114.7 |
| 4 | 50.4 | 10.2 |
| 6 | 51.2 | |
| 23 | 50.3 | |

MBTH.HCl is effectively decomposed after only two hours at 120° C., while NaCMBTH is still viable after six hours at the same temperature, and even retains most of its activity after 23 hours.

Example 4

Solubility Comparison

The solubility of MBTH.HCl was compared with that of NaCMBTH. One hundred mg samples of each of MBTH.HCl (Aldrich) and NaCMBTH were placed into test tubes. Water was added in 50 μ-L aliquots until the sample completely dissolved. The solubility of the compounds is shown in Table 2.

TABLE 2

| Compound | Water added | Solubility (mg/mL) |
|---|---|---|
| MBTH.HCl | 2900 μL | 34 |
| NaCMBTH | 1150 μL | 87 |

An identical experiment was performed using pH 7 buffer (phosphate, 0.1M) instead of water. The results are shown in Table 3.

TABLE 3

| Compound | Water added | Solubility (mg/mL) |
|---|---|---|
| MBTH.HCl | >9600 μL | <10 |
| NaCMBTH | 575 μL | 174 |

Example 5

Device for Quantitatively Determining Hydrogen Peroxide

An oven dried, three neck, 250-mL, round bottom flask was fitted with a stoppered addition funnel, condenser with tubing adapter to a nitrogen bubbler, and a stopper. A stirbar was placed into the flask. Under constant nitrogen purge, the cool, dry flask was placed into an ice/water bath. Twenty five grams of isocyanatopropyltriethoxysilane were introduced into the flask while the flask was flushed with nitrogen. The addition funnel was filled with twenty grams of an amine-functional aniline-type dye as the purge continued. The setup was then switched from nitrogen purge to nitrogen bubbler. The amine was added dropwise, one drop per second, via the addition funnel, while the contents of the flask were stirred. When addition was complete, the mixture was allowed to stir for ten minutes. The ice/water bath was removed and the contents were warmed to room temperature with stirring. The product should be used immediately, and must remain under nitrogen until used in the next step of the process. The product is a viscous, clear liquid.

Five hundred grams of silica gel and six liters of toluene were slurried in a ten liter, three neck, round bottom flask equipped with a reflux condenser and a stirring shaft. The amine-silane mixture just prepared was transferred all at once to the large flask containing the slurry. The small flask was rinsed with 500 mL of toluene and the rinse was added to the silica/silane slurry. The mixture was brought to reflux and refluxed with stirring for two hours. The slurry was cooled to room temperature.

The product was collected in a Buchner funnel. The product was placed into a large vessel and covered with four liters of toluene and stirred for 30 minutes. The finished product was air-dried.

Preparation of Analytical Film

A 12" by 5" swatch of polyester fabric (PeCap® from Tetko, Briarcliffe Manor, N.Y.) is attached to a glass plate using double-stick tape. A paste containing 0.25 gram of the dyed matrix as prepared above, 125 μL of 25 mg/mL NaCMBTH in methanol, 100 μL of 18 mg/1.5 mL water, 200 μL of anhydrous methanol and 400 μL of polyvinyl acetate, medium MW, 12% methanolic solution, a film-forming polymer, was placed at one end of the swatch and a film is drawn down onto the fabric using a film-casting knife (Paul N. Gardner Company, Pompano Beach, Fla.) set at 1 mil (0.001 inch). This film is dried at 40° C. for ten minutes, and then 5 mm wide strips are cut and heat sealed with polyester top and bottom films to form very precise flow channels.

Determination of Hydrogen Peroxide

Plasma with varying concentrations of hydrogen peroxide is introduced into the channels prepared as above. As the sample flows through the channels, dark blue color bars form with sharp color fronts. The length of the color bars is proportional to the concentration of hydrogen peroxide in each sample.

Any recitation of a preferred range is to be deemed to include a description of the included subranges. Any recitation of a multimember class of elements is to be deemed to include a description of the possible subclasses. Any recitation of individual embodiments is to be deemed to also include a description of all possible combinations of said embodiments. All references, including prior patent applications cited (if any), are to be deemed incorporated in their entirety by reference.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. Water soluble salts of 6-carboxy-3-methylbenzothiazolone hydrazone hydrate.

2. The water soluble salts of claim 1 selected from the group consisting of sodium salt, potassium salt, and ammonium salt.

3. A dye formed from the reaction between a soluble salt of 6-carboxy-3-methylbenzothiazolone hydrazone hydrate and a substituted or unsubstituted aniline dye.

4. A dye according to claim 3 wherein the aniline dye is selected from the compounds of the formula

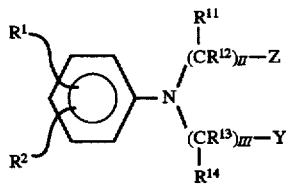

wherein $R^1$ and $R^2$ are selected from the group consisting of hydrogen; $C_1$–$C_9$ alkyl, $C_1$–$C_9$ alkoxy; $NR^3R^4$ and $R^3$ and $R^4$ are selected from the group consisting of hydrogen, $C_1$–$C_9$ alkyl, aryl, and heteroaryl; F; Cl; Br; I; $COOR^5$ wherein $R^5$ is selected from the group consisting of hydrogen, $C_1$–$C_9$ alkyl, aryl, and heteroaryl; CN; $CONR^6R^7$ where $R^6$ and R7 are selected from the group consisting of hydrogen and $C_1$–$C_9$ aryl, alkyl, and heteroaryl; aryl; aryloxy; heteroaryl; heteroaryloxy; and $R^{11}$, $R^{12}$, $R^{13}$ and $R^{14}$ are selected from the group consisting of hydrogen, $C_1$–$C_9$ alkyl; $C_1$–$C_9$ alkoxy; $NR^{15}R^{16}$ wherein $R^{15}$ and $R^{16}$ are selected from the group consisting of hydrogen; $C_1$–$C_9$ alkyl, aryl, and heteroaryl; CN; $CONR^{18}R^{19}$ where $R^{18}$ and $R^{19}$ are selected from the group consisting of hydrogen; $C_1$–$C_9$ alkyl, aryl, and heteroaryl; aryl; aryloxy; heteroaryl; heteroaryloxy;

n is an integer of from 0 to 10;

Z and Y are each selected from the group consisting of hydrogen; OH, SH; $COOR^8$ where $R^8$ is hydrogen, $C_1$–$C_9$ alkyl, aryl or heteroaryl; $NR^{20}NHR^{21}$ where $R^{20}$ and $R^{21}$ are hydrogen, $C_1$–$C_9$ alkyl, aryl, or heteroaryl; and at least one of Z and Y is $COOR^8$, $CN'NR^9R^{10}$ or $NR^{20}NHR^{21}$.

5. A dye according to claim 4 wherein the aniline dye is selected from the group consisting of N,N-(biscarboxymethyl)aniline; N,n-(biscarboxymethyl)-4-methoxyaniline; N,N-(bis-beta-carboxyethyl)aniline; N-ethyl-N-phenyl glycine; N-ethyl-N-carboxyethylaniline; N-phenylpiperidinyl succinate; N-ethylanilinopropaneamine; N-methylanilinopropaneamine; N-methyl-N-carboxyethylaniline; N,N-(bis-beta-carboxyethyl)2,5-dimethylaniline; N-beta-carboxyethylaminobenzoic acid.

6. A dye-forming composition comprising a water soluble salt of 6-carboxy-3-methylbenzothiazolone hydrazone hydrate, a substituted or unsubstituted aniline compound.

7. A reagent according to claim 6 wherein the aniline dye is selected from the group consisting of compounds of the formula

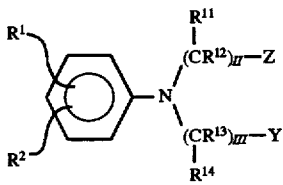

wherein $R^1$ and $R^2$ are selected from the group consisting of hydrogen; $C_1$–$C_9$ alkyl, $C_1$–$C_9$ alkoxy; $NR^3R^4$ where $R^3$ and $R^4$ are selected from the group consisting of hydrogen, $C_1$–$C_9$ alkyl, aryl, and heteroaryl; F; Cl; Br; I; $COOR^5$ wherein $R^5$ is selected from the group consisting of hydrogen, $C_1$–$C_9$ alkyl, aryl, and heteroaryl; CN; $CONR^6R^7$ where $R^6$ and $R^7$ are selected from the group consisting of hydrogen and $C_1$–$C_9$ aryl, alkyl, and heteroaryl; aryl; aryloxy; heteroaryl; heteroaryloxy; and $R^{11}$, $R^{12}$, $R^{13}$ and $R^{14}$ are selected from the group consisting of hydrogen, $C_1$–$C_9$ alkyl; $C_1$–$C_9$ alkoxy; $NR^{15}R^{16}$ wherein $R^{15}$ and R16 are selected from the group consisting of hydrogen; $C_1$–$C_9$ alkyl, aryl, and heteroaryl; CN; $CONR^{18}R^{19}$ where $R^{18}$ and $R^{19}$ are selected from the group consisting of hydrogen; $C_1$–$C_9$ alkyl, aryl, and heteroaryl; aryl; aryloxy; heteroaryl; heteroaryloxy;

n is an integer of from 0 to 10;

Z and Y are each selected from the group consisting of hydrogen; OH, SH; $COOR^8$ where $R^8$ is hydrogen, $C_1$–$C_9$ alkyl, aryl or heteroaryl; $NR^{20}NHR^{21}$ where $R^{20}$ and $R^{21}$ are hydrogen, $C_1$–$C_9$ alkyl, aryl, or heteroaryl; and at least one of Z and Y is $COOR^8$, $CN'NR^9R^{10}$ or $NR^{20}NHR^{21}$.

8. A dye-forming composition according to claim 7 wherein the aniline dye is selected from the group consisting of N,N-(biscarboxymethyl)aniline; N,n-(biscarboxymethyl)-4-methoxyaniline; N,N-(bis-beta-carboxyethyl)aniline; N-ethyl-N-phenyl glycine; N-ethyl-N-carboxyethylaniline; N-phenylpiperidinyl succinate; N-ethylanilinopropaneamine; N-methylanilinopropaneamine; N-methyl-N-carboxyethylaniline; N,N-(bis-beta-carboxyethyl)2,5-dimethylaniline; N-beta-carboxyethylaminobenzoic acid.

9. A reagent for detection of hydrogen peroxide comprising the dye-forming composition of claim 6 and a peroxidase.

10. A diagnostic test kit for the determination of hydrogen peroxide, said kit comprising a container means containing:

a dye-forming composition according to claim 6 comprising:

(1) a water soluble salt of 6-carboxy-3-methyl benzothiazolone hydrazone hydrate; and (2) a substituted or unsubstituted aniline dye which reacts with said water-soluble salt of 6-carboxy-3-methylbenzothiazolone hydrazone hydrate to produce a colored dye.

11. A diagnostic test kit according to claim 10 wherein the aniline dye is selected from the group consisting of compounds of the formula

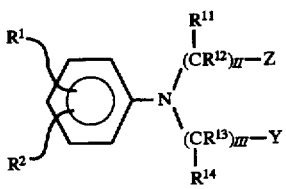

wherein $R^1$ and $R^2$ are selected from the group consisting of hydrogen; $C_1$–$C_9$ alkyl, $C_1$–$C_9$ alkoxy; $NR^3R^4$ where $R^3$ and $R^4$ are selected from the group consisting of hydrogen, $C_1$–$C_9$ alkyl, aryl, and heteroaryl; F; Cl; Br; I; $COOR^5$ wherein $R^5$ is selected from the group consisting of hydrogen, $C_1$–$C_9$ alkyl, aryl, and heteroaryl; CN; $CONR^6R^7$ where $R^6$ and $R^7$ are selected from the group consisting of hydrogen and $C_1$–$C_9$ aryl, alkyl, and heteroaryl; aryl; aryloxy; heteroaryl; heteroaryloxy; and $R^{11}$, $R^{12}$, $R^{13}$ and $R^{14}$ are selected from the group consisting of hydrogen, $C_1$–$C_9$ alkyl; $C_1$–$C_9$ alkoxy; $NR^{15}R^{16}$ wherein $R^{15}$ and $R^{16}$ are selected from the group consisting of hydrogen; $C_1$–$C_9$ alkyl, aryl, and heteroaryl; CN; $CONR^{18}R^{19}$ where $R^{18}$ and $R^{19}$ are selected from the group consisting of hydrogen; $C_1$–$C_9$ alkyl, aryl, and heteroaryl; aryl; aryloxy; heteroaryl; heteroaryloxy;

n is an integer of from 0 to 10;

Z and Y are each selected from the group consisting of hydrogen; OH, SH; $COOR^8$ where $R^8$ is hydrogen, $C_1$–$C_9$ alkyl, aryl or heteroaryl; $NR^{20}NHR^{21}$ where $R^{20}$ and $R^{21}$ are hydrogen, $C_1$–$C_9$ alkyl, aryl, or heteroaryl; and at least one of Z and Y is $COOR^8$, $CN'NR^9R^{10}$ or $NR^{20}NHR^{21}$.

12. A diagnostic test kit according to claim 11 wherein the aniline dye is selected from the group consisting of N,N-(biscarboxymethyl)aniline; N,n-(biscarboxymethyl)-4-methoxyaniline; N,N-(bis-beta-carboxyethyl)aniline; N-ethyl-N-phenyl glycine; N-ethyl-N-carboxyethylaniline; N-phenylpiperidinyl succinate; N-ethylanilinopropaneamine; N-methylanilinopropaneamine; N-methyl-N-carboxyethylaniline; N,N-(bis-beta-carboxyethyl)2,5-dimethylaniline; N-beta-carboxyethylaminobenzoic acid.

13. A diagnostic test kit according to claim 10 further including a peroxidase.

14. A method for determining hydrogen peroxide or an analyte which reacts to produce hydrogen peroxide in an aqueous liquid, said method comprising the steps of:

(a) in the presence of a substance having peroxidative activity, physically contacting a sample of a liquid with a dye forming composition according to claim 6, wherein if hydrogen peroxide or an analyte which reacts to form hydrogen peroxide in an aqueous liquid is present in the sample, the dye forming composition will react with said hydrogen peroxide or an analyte which reacts to form hydrogen peroxide in an aqueous liquid; and (b) detecting dye formed from the reaction of the dye forming composition with the substance having peroxidative activity.

15. A method according to claim 14 wherein the aniline dye is selected from the group consisting of compounds of the formula

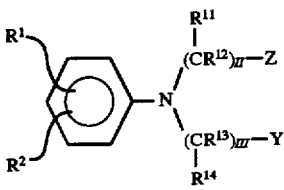

wherein $R^1$ and $R^2$ are selected from the group consisting of hydrogen; $C_1$–$C_9$ alkyl, $C_1$–$C_9$ alkoxy; $NR^3R^4$ where $R^3$ and $R^4$ are selected from the group consisting of hydrogen, $C_1$–$C_9$ alkyl, aryl, and heteroaryl; F; Cl; Br; I; $COOR^5$ wherein $R^5$ is selected from the group consisting of hydrogen, $C_1$–$C_9$ alkyl, aryl, and heteroaryl; CN; $CONR^6R^7$ where $R^6$ and $R^7$ are selected from the group consisting of hydrogen and $C_1$–$C_9$ aryl, alkyl, and heteroaryl; aryl; aryloxy; heteroaryl; heteroaryloxy; and $R^{11}$, $R^{12}$, $R^{13}$ and $R^{14}$ are selected from the group consisting of hydrogen, $C_1$–$C_9$ alkyl; $C_1$–$C_9$ alkoxy; $NR^{15}R^{16}$ wherein $R^{15}$ and $R^{16}$ are selected from the group consisting of hydrogen; $C_1$–$C_9$ alkyl, aryl, and heteroaryl; CN; $CONR^{18}R^{19}$ where $R^{18}$ and $R^{19}$ are selected from the group consisting of hydrogen; $C_1$–$C_9$ alkyl, aryl, and heteroaryl; aryl; aryloxy; heteroaryl; heteroaryloxy;

n is an integer of from 0 to 10;

Z and Y are each selected from the group consisting of hydrogen; OH, SH; $COOR^8$ where $R^8$ is hydrogen, $C_1$–$C_9$ alkyl, aryl or heteroaryl; $NR^{20}NHR^{21}$ where $R^{20}$ and $R^{21}$ are hydrogen, $C_1$–$C_9$ alkyl, aryl, or heteroaryl; and at least one of Z and Y is $COOR^8$, $CN'NR^9R^{10}$ or $NR^{20}NHR^{21}$.

16. A method according to claim 15 wherein the aniline dye is selected from the group consisting of N,N-(biscarboxymethyl) aniline; N,N-(biscarboxymethyl)-4-methoxyaniline; N,N-(bis-beta-carboxyethyl)aniline; N-ethyl-N-phenyl glycine; N-ethyl-N-carboxyethylaniline; N-phenylpiperidinyl succinate; N-ethylanilinopropaneamine; N-methylanilinopropaneamine; N-methyl-N-carboxyethylaniline; N,N-(bis-beta-carboxyethyl)2,5-dimethylaniline; N-beta-carboxyethylaminobenzoic acid.

17. A method for determining hydrogen peroxide or an analyte which reacts to produce hydrogen peroxide in an aqueous liquid comprising the method according to claim 14 wherein the dye forming composition further includes a peroxidase.

18. In a method for determining hydrogen peroxide or an analyte which reacts to produce hydrogen peroxide, the improvement comprising using as a color-forming agent a combination of 6-carboxy-3-methylbenzothiazolone hydrazone hydrate and an aniline dye.

19. The method according to claim 18 wherein the aniline dye is selected from the group consisting of compounds of the formula

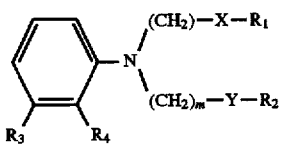

wherein $R^1$ and $R^2$ are selected from the group consisting of hydrogen; $C_1-C_9$ alkyl, $C_1-C_9$ alkoxy; $NR^3R^4$ where $R^3$ and $R^4$ are selected from the group consisting of hydrogen, $C_1-C_9$ alkyl, aryl, and heteroaryl; F; Cl; Br; I; $COOR^5$ wherein $R^5$ is selected from the group consisting of hydrogen, $C_1-C_9$ alkyl, aryl, and heteroaryl; CN; $CONR^6R^7$ where $R^6$ and $R^7$ are selected from the group consisting of hydrogen and $C_1-C_9$ aryl, alkyl, and heteroaryl; aryl; aryloxy; heteroaryl; heteroaryloxy; and $R^{11}$, $R^{12}$, $R^{13}$ and $R^4$ are selected from the group consisting of hydrogen, $C_1-C_9$ alkyl; $C_1-C_9$ alkoxy; $NR^{15}R^{16}$ wherein $R^{15}$ and $R^{16}$ are selected from the group consisting of hydrogen; $C_1-C_9$ alkyl, aryl, and heteroaryl; CN; $CONR^{18}R^{19}$ where $R^{18}$ and $R^{19}$ are selected from the group consisting of hydrogen; $C_1-C_9$ alkyl, aryl and heteroaryl; aryl; aryloxy; heteroaryl; heteroaryloxy;

n is an integer of from 0 to 10;

Z and Y are each selected from the group consisting of hydrogen; OH, SH; $COOR^8$ where $R^8$ is hydrogen, $C_1-C_9$ alkyl, aryl or heteroaryl; $NR^{20}NHR^{21}$ where $R^8$ and $R^{21}$ are hydrogen, $C_1-C_9$ alkyl, aryl, or heteroaryl; and at least one of Z and Y is $COOR^8$, $CN'NR^9R^{10}$ or $NR^{20}NHR^{21}$.

20. A method according to claim 18 wherein the aniline dye is selected from the group consisting of N,N (biscarboxymethyl)aniline; N,N-(biscarboxymethyl)-4-methoxyaniline; N,N-(bis-beta-carboxyethyl)aniline; N-ethyl-N-phenyl glycine; N-ethyl-N-carboxyethylaniline; N-phenylpiperidinyl succinate; N-ethylanilinopropaneamine; N-methylanilinopropaneamine; N-methyl-N-carboxyethylaniline; N,N-(bis-beta-carboxyethyl) 2,5-dimethylaniline; N-beta-carboxyethylaminobenzoic acid.

\* \* \* \* \*